(12) United States Patent
Ohara et al.

(10) Patent No.: US 8,741,323 B2
(45) Date of Patent: Jun. 3, 2014

(54) EXTERNAL SKIN AGENT COMPRISING MODIFIED CLAY FOR PREVENTING INFLAMMATION

(75) Inventors: Yasuhiro Ohara, Kanagawa (JP); Masashi Suzuki, Kanagawa (JP); Norikazu Takano, Tokyo (JP); Shunpei Mitsuyama, Tokyo (JP)

(73) Assignee: Pola Chemical Industries Inc., Shizuoka (JP)

( * ) Notice: Subject to any disclaimer, the term of this patent is extended or adjusted under 35 U.S.C. 154(b) by 1547 days.

(21) Appl. No.: 11/722,338

(22) PCT Filed: Nov. 25, 2005

(86) PCT No.: PCT/JP2005/022139
§ 371 (c)(1),
(2), (4) Date: Jun. 20, 2007

(87) PCT Pub. No.: WO2006/067945
PCT Pub. Date: Jun. 29, 2006

(65) Prior Publication Data
US 2010/0003210 A1      Jan. 7, 2010

(30) Foreign Application Priority Data
Dec. 22, 2004    (JP) .................................. 2004-371895

(51) Int. Cl.
*A61Q 19/00* (2006.01)
(52) U.S. Cl.
USPC ......................................... 424/401; 514/770
(58) Field of Classification Search
None
See application file for complete search history.

(56) References Cited

U.S. PATENT DOCUMENTS

| | | | |
|---|---|---|---|
| 4,446,051 A | | 5/1984 | Berthod et al. |
| 5,036,108 A | * | 7/1991 | Asahi et al. ................... 514/772 |
| 5,422,361 A | * | 6/1995 | Munayyer et al. ............ 514/408 |
| 5,665,367 A | | 9/1997 | Burger et al. |
| 6,372,234 B1 | * | 4/2002 | Deckers et al. ............... 424/401 |
| 2003/0049282 A1 | * | 3/2003 | Aronson et al. .............. 424/401 |
| 2004/0001897 A1 | | 1/2004 | Amano et al. |
| 2004/0175344 A1 | | 9/2004 | Woller |

FOREIGN PATENT DOCUMENTS

| | | |
|---|---|---|
| JP | 61-129033 | 6/1986 |
| JP | 61-212321 | 9/1986 |
| JP | 62-216635 | 9/1987 |
| JP | 08-217695 | 8/1996 |
| JP | 2001-048721 | 2/2001 |
| JP | 2003-192525 | 12/2001 |
| JP | 2003-026529 | 1/2003 |
| JP | 2003-26608 | 1/2003 |
| JP | 2003-095956 | 4/2003 |
| JP | 2003-113069 | 4/2003 |
| JP | 2003-160462 | 6/2003 |
| WO | WO 97/26917 | 7/1997 |
| WO | WO 00/32155 | 6/2000 |
| WO | WO 03/051979 | 6/2003 |
| WO | WO 2005/039517 | 5/2005 |

OTHER PUBLICATIONS

Fowler, A Skin Moisturizing Cream Containing Quaternium-18-Bentonite Effectively Improves Chronic Hand Dermatitis, J Cutan Med Surg 2001; 201-205 (2001).*
Lee, Phospholipid Polymer, 2-methacryloyloxyethyl phosphorylcholine and its skin barrier function, Arch Pharm Res vol. 27, No. 11, 1177-1182, Nov. 30, 2004.*
Atopic Dermatitis, Merck Manual. Sep. 2009.*
International Search Report dated Mar. 21, 2006.
Watanabe, et al. "Functional Analyses of the Superficial Stratum Corneum in Atopic Xerosis," *Arch. Dermatol.*, vol. 127, pp. 1689-1692, 1991.
Office Action dated Jan. 10, 2012 and issued to corresponding Japanese patent application No. 2007-529296.

* cited by examiner

*Primary Examiner* — Jyothsna Venkat
(74) *Attorney, Agent, or Firm* — Knobbe, Martens, Olson & Bear LLP

(57) ABSTRACT

To provide An external skin agent that prevents onset of atopic skin inflammations and is low irritant to skin, which is characterized by including: 1) clay modified by a compound having a quaternary amino group; and 2) a polymer or copolymer that has a side chain including a structure similar to a biological component.

5 Claims, 2 Drawing Sheets

** : P < 0.01 VS. NO TREATMENT GROUP (Dunnett test)

\# : P < 0.05 VS. WHITE PETROLATUM GROUP (Tukcy test)

EXTERNAL SKIN AGENT COMPRISING MODIFIED CLAY FOR PREVENTING INFLAMMATION

RELATED APPLICATIONS

This is the U.S. National Phase under 35 U.S.C. §371 of International Application PCT/JP2005/022139, filed Nov. 25, 2005, which claims priority of JP 2004-371895, filed Dec. 22, 2004.

TECHNICAL FIELD

The present invention relates to an external skin agent, specifically to an external skin agent that has an effect to prevent inflammations.

BACKGROUND ART

In recent years, patients who suffer from atopic dermatitis or sensitive skin and have bad prognosis, the atopic dermatitis or sensitive skin being possibly caused by, for example, remarkable westernization in diet habits and rapid increase in social stress, have increased rapidly. In many cases, the skin inflammations (atopic skin inflammation or the like) of those patients are not adequately treated by treatments with anti-inflammatory skin medicines for external use or anti-inflammatory quasi drugs that have been conventionally used.

For such inflammations, in some cases, cosmetics in which polyalcohols that are general-purpose materials for cosmetics are richly incorporated are more effective than the anti-inflammatory skin medicines for external use or anti-inflammatory quasi drugs, or medical agents for other purposes such as 5-HT antagonist are effective (see, for example, Patent Document 1, Patent Document 2, and Patent Document 3).

However, an agent having an effect to adequately treat atopic skin inflammation or the like has not been found yet. Therefore, many atopic skin inflammations are palliatively treated by a combination of external administration of a steroid anti-inflammatory agent such as dexamethasone or prednisolone with an immunosuppressive agent such as cyclosporine, antioxidant such as ascorbic acid, or 5-HT antagonist, and patients suffering from atopic skin inflammations are forced to resist the disadvantages. Accordingly, it has been desired to develop a preparation to prevent inflammation for external use that sufficiently exerts its effect for atopic dermatitis or the like even if the preparation is independently used.

Moreover, it has been feared that those preparations have side effects such as contamination in affected areas by bacteria and ultraviolet hazard, and there has been a problem in use of them for treating atopic skin inflammations over a long period of time.

The above-described conventional therapeutic agents for atopic skin inflammations are agents for treating developed atopic skin inflammations. Meanwhile, means for effectively preventing onset of atopic skin inflammations have not been known. In general, it is known that alleviations of developed inflammations are difficult, and it is significant to provide an agent capable of preventing onset of atopic skin inflammations.

Meanwhile, it is believed that an external skin agent that lowers a representative value for moisture retention such as water loss value is effective for a general skin inflammation. It is published that there is also correlation between an atopic skin inflammation and the water loss value (Non-Patent Document 1). However, the therapeutic effect of the external skin agents that lowers a representative value for moisture retention such as water loss value to the atopic skin inflammation is low. Therefore, it has been desired to develop an external skin agent that has functional mechanism different from those of conventional skin preparations for external use.

It is known that a polymer including a group similar to phosphorylcholine that is one of a structure similar to a biological component is included in an anti-inflammatory external skin agent together with an anti-inflammatory medicine before use (see, for example, Patent Document 4). The anti-inflammatory external skin agent is known to have effects to impair moisture-retention ability to skin and be low irritant to skin.

It is known that when bentonite is included in an inflammatory external skin agent, a system of the inflammatory external skin agent may be stabilized (see, for example, Patent Document 5).

Meanwhile, it is known that when organically modified bentonite is included in an oil cosmetic, it may act as a thickener in an oil phase (see, for example, Patent Document 6).

[Patent Document 1] JP-A-2003-95956
[Patent Document 2] JP-A-08-217695
[Patent Document 3] JP-A-2001-48721
[Patent Document 4] JP-A-2003-26608
[Patent Document 5] JP-A-2003-113069
[Patent Document 6] JP-A-2003-26529
[Non-Patent Document 1] Watanabe, M., Tagami, H., Horii, I., Takahashi, M., Kligman, A. M. Functional analyses of the superficial stratum corneum in atopic xerosis. Arch. Dermatol. 127, 1689-1692, 1991

DISCLOSURE OF THE INVENTION

Problems to be Solved by the Invention

The present invention has been accomplished under the circumstances, and it is an object of the present invention to provide a preparation that significantly inhibits onset of atopic skin inflammations and is effective for preventing onset of the inflammations.

It is a further object of the present invention to provide the above-described preparation that is low irritant and may be used on a daily basis.

It is a further object of the present invention to provide an external skin agent that has an effect to prevent onset of atopic skin inflammations and has an anti-inflammatory effect.

Means for Solving the Problems

The inventors of the present invention have made extensive studies to search a preparation that may significantly inhibit onset of atopic skin inflammations, is effective for preventing onset of the inflammations, is low irritant, and may be used on a daily basis. As a result, they have found out a preparation that not only has a low representative value for moisture retention such as water loss value but also has a mechanism to inhibit atopic skin inflammations different from that of a conventional external skin agent, and they have found out that the preparation has the above-described effects, thereby completing the present invention.

That is, the present invention is as follows.

(1) An external skin agent, characterized by including: 1) clay modified by a compound having a quaternary amino group; and 2) a polymer or copolymer that has a side chain including a structure similar to a biological component.

(2) An external skin agent according to the above item (1), in which the clay is bentonite, montmorillonite, or kaolinite modified by a compound having a quaternary amino group.

(3) An external skin agent according to the above item (1) or (2), in which the compound having a quaternary amino group is dimethyl distearyl ammonium chloride.

(4) An external skin agent according to any one of the above items (1) to (3), in which the structure similar to a biological component is a structure similar to a saccharide, a structure similar to an amino acid, or a structure similar to a phospholipid.

(5) An external skin agent according to any one of the above items (1) to (4), in which the structure similar to a biological component is a glucosyloxyethyl group, a lysine residue, or a trimethylaminoethoxyphosphoethyl group.

(6) An external skin agent according to any one of the above items (1) to (5), in which the polymer or copolymer is a polymer or copolymer that is obtainable by addition polymerization of a vinyl monomer that includes one or two or more kinds of acrylic acids or methacrylic acids each represented by the following formula (X):

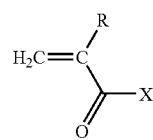

(X)

(in the formula (X), R represents a hydrogen atom or a methyl group, and X represents a group including a structure similar to a biological component).

(7) An external skin agent according to any one of the above items (1) to (6), in which the polymer or copolymer is one or two or more kinds selected from the group consisting of polyglucosyloxyethyl methacrylate, polymethacryloyl lysine, polymethacryloyloxyethyl phosphorylcholine, a methacryloyloxyethyl phosphorylcholine-butyl methacrylate copolymer, and a methacryloyloxyethyl phosphorylcholine-stearyl methacrylate copolymer.

(8) An external skin agent according to any one of the above items (1) to (7), further including a silicone.

(9) An external skin agent according to the above item (8), in which the silicone includes at least three kinds of silicones including a volatile silicone, a low-viscosity silicone, and a middle-viscosity silicone.

(10) An external skin agent according to the above item (8), in which the silicone includes an alkylenoxide methylsiloxane copolymer, and the content of the alkylenoxide methylsiloxane copolymer is 0.1 to 10% by mass with respect to the total amount of the external skin agent.

(11) An external skin agent according to the above item (8), in which the silicone includes: 1) at least three kinds of dimethicones or phenylmethicones including a volatile silicone, a low-viscosity silicone, and a middle-viscosity silicone; and 2) an alkylenoxide methylsiloxane copolymer.

(12) An external skin agent according to any one of the above items (1) to (11), further including a sucrose fatty acid ester.

(13) An external skin agent according to any one of the above items (1) to (12), further including one or two or more kinds of anti-inflammatory components selected from the group consisting of alcohol extract of Compositae *Arctium lappa*, alcohol extract of Araliaceae *Panax Notoginseng*, alcohol extract of Betulaceae *Betula maximowicziana*, alcohol extract of Leguminosae *Sophora flavescens*, alcohol extract of Lamiaceae *Salvia officinalis*, alcohol extract of Juglandaceae *Engelhardtia chrysolepis*, alcohol extract of Compositae *Achillea millefolium*, alcohol extract of Lamiaceae *Rosmarinus officinalis*, glycyrrhizinic acid and/or a salt thereof, glycyrrhetinic acid ester, ursolic acid and/or a salt thereof, ursolic acid ester, a glycoside of plant steroid (phytosterol), indomethacin, ketoprofen, ketotifen, bufexamac, dexamethasone, prednisolone, beclomethasone, betamethasone, hydrocortisol, and tacrolimus.

(14) An external skin agent according to any one of the above items (1) to (13), which is in the form of a water-in-oil emulsion.

(15) An external skin agent according to any one of the above items (1) to (14), which is used for alleviating or preventing atopic dermatitis.

Effect of the Invention

According to the present invention, there may be provided an external skin agent that may significantly inhibit onset of atopic skin inflammations, is effective for preventing onset of the inflammations, is low irritant, and may be used on a daily basis.

BEST MODE FOR CARRYING OUT THE INVENTION

Figure 1:
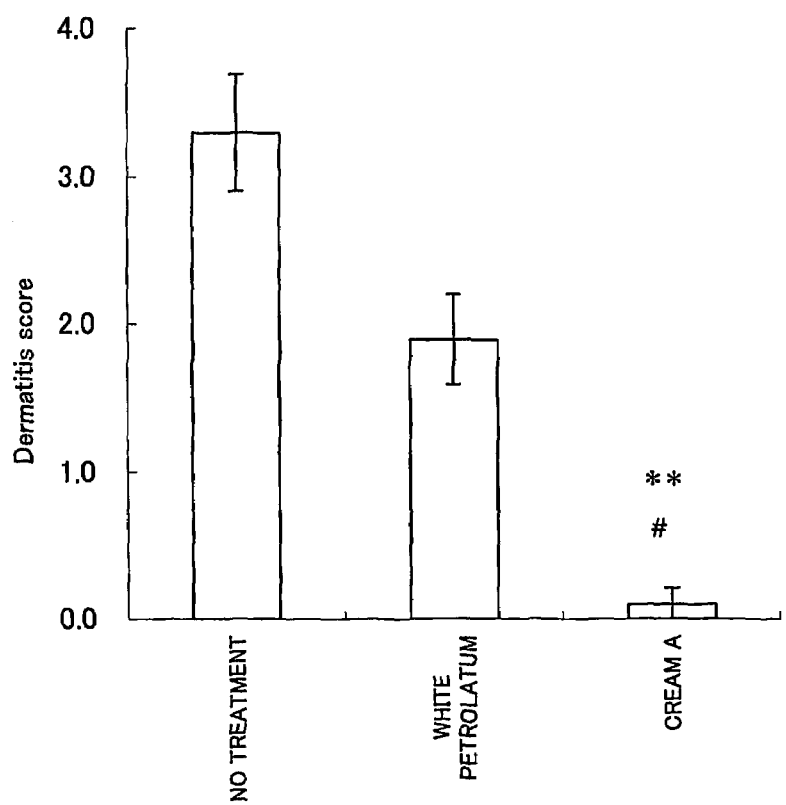
FIG. 1 is a graph showing the results of Test Example 1-1.

As described above, the external skin agent of the present invention includes clay modified by a compound having a quaternary amino group (hereinafter also referred to as "modified clay") and a polymer or copolymer that has a side chain including a structure similar to a biological component, and it may further include any other ingredient such as a silicone, anti-inflammatory ingredient, or sucrose fatty acid ester.

<1. Clay Modified by Compound Having Quaternary Amino Group>

The external skin agent of the present invention is characterized by including clay modified by a compound having a quaternary amino group. The compound that modifies clay and has a quaternary amino group is not particularly limited, but an example thereof includes a compound referred to as quaternium. The quaternium is a substituted quaternary ammonium salt having a low molecular weight and a material for cosmetics that has been registered with International Nomenclature Cosmetic Ingredient (INCI).

Moreover, the compound that modifies clay and has a quaternary amino group is preferably a quaternium compound that is included in a conventional external skin agent out of the quaternium compounds. Preferable examples of the quaternium compound used in a conventional external skin agent include stearyl trimethyl ammonium chloride and dimethyl distearyl ammonium chloride. Stearyl trimethyl ammonium chloride, dimethyl distearyl ammonium chloride, or the like may form a stable water-in-oil emulsion structure together with clay, so that it is estimated that those compounds may enhance the skin barrier function of the external skin agent of the present invention.

On the other hand, clay to be modified by a compound having a quaternary amino group (unmodified clay) may be used without particular limitation as long as it is clay that is included in a conventional external skin agent. Examples of the clay that is included in a conventional external skin agent include: smectite-based bentonite and montmorillonite; kaolinite; illite; marine clay; desert rose clay; and pascalite.

Of those, preferable is bentonite, montmorillonite, which involves montmorillonite, hectorite, nontronite and alluminiasaponite, or kaolinite, which is estimated to stabilize a water-in-oil emulsion structure and improve a barrier function of skin suffering from atopic skin inflammation.

The "modification" of clay by a compound having a quaternary amino group refers to, for example, insertion of a compound having a quaternary amino group between silicate layers in clay, but it is not particularly limited thereto and refers to making changes in physical properties of clay by a compound having a quaternary amino group. Preferably, such modification generates paired ions (ion bonds) in the quaternary amino group in a compound having a quaternary amino group and an anionic portion in clay, to thereby yield clay that has a surfactant ability and is a complex formed by associating a hydrophobic group and a hydrophilic group in a mild state.

Hereinafter, there will be described one example of a method of producing clay modified by a compound having a quaternary amino group to be included in the external skin agent of the present invention.

The above-described unmodified clay is dispersed in a dispersion medium. The dispersion medium is preferably a water-based solvent and may be water. Moreover, the dispersion solution including the dispersed unmodified clay is added with a compound having a quaternary amino group, and the mixture is stirred well. The compound having a quaternary amino group may be added after being dissolved in water. The amount of a compound having a quaternary amino group to be added is preferably 0.1 to 20% by mass, more preferably 0.5 to 15% by mass with respect to the amount of the dispersed unmodified clay because the compound stabilizes a water-in-oil emulsion structure of the external skin agent of the present invention and improve the barrier function of skin suffering from atopic skin inflammations.

After stirring, the dispersoids are collected with a filter paper, and dewatering and drying are performed, to thereby yield modified clay in the present invention. Alternatively, the dispersion medium is removed by vacuum concentration without collection of the dispersoids with a filter paper, and then drying is performed, to thereby yield modified clay in the present invention.

The resultant modified clay is preferably pulverized into a desired size (preferably, it has a particle size of 1 to 1,000 μm) and is included in the external skin agent of the present invention.

The modified clay in the present invention may be prepared as described above and used, or commercially available modified clay may also be used. Some commercially available modified clays are used as skin preparations for external use or the like such as cosmetics. An example of the commercially available modified clay includes dimethyl distearyl ammonium chloride-modified hectorite that is marketed as "Bentone 38V" from Elementis.

The modified clay in the present invention promotes emulsification of the external skin agent of the present invention, has an effect to stabilize an emulsification state, and synergistically exerts an anti-inflammatory effect together with a polymer or copolymer that has a side chain including a structure similar to a biological component described below.

Hereinafter, production examples of the modified clay in the present invention will be shown.

Production Example 1

95 parts by mass of kaolin was dispersed in 500 parts by mass of water, and 100 parts by mass of 5% by mass stearyl trimethyl ammonium chloride aqueous solution was added thereto. After having been stirred well, the mixture was concentrated under reduced pressure and then dried while being heated to 40° C. under reduced pressure. The resultant dried product was pulverized by a dry ball mill. The resultant pulverized product was further pulverized by a pulverizer mounted with a screen having 0.9 mm circular holes, and the second aggregates were crushed, to thereby yield particles each having a size of the primary particle. The resultant organically modified kaolinite was used in Examples below.

Production Example 2

95 parts by mass of montmorillonite was dispersed in 500 parts by mass of water, and 100 parts by mass of 5% bymass tributyl ammonium chloride aqueous solution was added thereto. After having been stirred well, the mixture was concentrated under reduced pressure and then dried while being heated to 40° C. under reduced pressure. The resultant dried product was pulverized by a dry ball mill. The resultant pulverized product was further pulverized by a pulverizer mounted with a screen having 0.9 mm circular holes, and the second aggregates were crushed, to thereby yield particles each having a size of the primary particle. The resultant organically modified montmorillonite was used in Examples below.

<2. Polymer or Copolymer Having Side Chain Including Structure Similar to Biological Component>

The external skin agent of the present invention includes a polymer or copolymer (hereinafter also collectively referred to as "(co)polymer") as an essential component. The (co)polymer that is included in the external skin agent of the present invention has a main chain having continuous carbon atom-carbon atom bonds like a vinyl polymer and a side chain including a structure similar to a biological component.

The (co)polymer that is included in the external skin agent of the present invention is obtainable by single polymerization or copolymerization of a vinyl monomer capable of addition polymerization. The vinyl monomer capable of addition polymerization is not particularly limited, but examples thereof include (meth)acrylic acids (esters), styrenes, and vinyl alcohols. Of those, preferable are acrylic acid, methacrylic acid, alkyl acrylate, and alkyl methacrylate.

The side chain of the (co)polymer that is included in the external skin agent of the present invention has a structure similar to a biological component. Herein, the biological component means a saccharide, protein, peptide, amino acid, phospholipid, sphingoglycolipid, sphingophospholipid, etc that is essential to the structure of a living body. The structure similar to a biological component means a structure in which a partial structure of the biological component or a part of the partial structure thereof has varied. Herein, "a part varies" means that the part is subjected to glycosidation, alkylation, alkenylation, arylation, acylation, amidation, phosphorylation, (alkyl)amination, or phosphorylation.

The structure similar to a biological component of the side chain of the (co)polymer in the present invention is preferably a structure similar to a saccharide, a structure similar to an amino acid, or a structure similar to a phospholipid. An example of the structure similar to a saccharide includes a glucosyloxyethyl group; an example of the structure similar to an amino acid includes a lysine residue; an examples of the structure similar to a phospholipid includes a trimethylaminoethoxyphosphoethyl group.

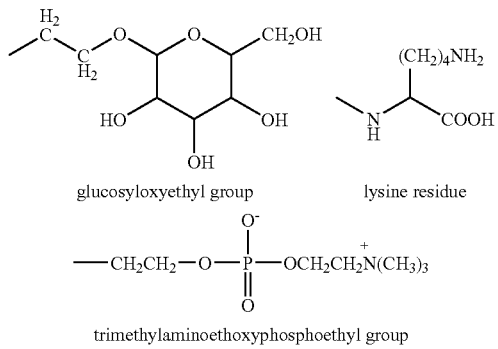

As described above, a (co)polymer to be included in the external skin agent of the present invention is produced by (co)polymerization of vinyl monomers. In fact, at least a part of vinyl monomers to be (co)polymerized are modified into a vinyl monomer in which a structure similar to a biological component is appropriately inserted, to thereby yield a (co)polymer that has a side chain including a structure similar to a biological component.

One example of a method of producing a (co)polymer to be included in the external skin agent of the present invention will be described below.

There is obtained the above-described vinyl monomer in which a structure similar to a biological component is inserted. Examples of the vinyl monomer in which a structure similar to a biological component is inserted include an acrylic acid and methacrylic acid each represented by the following formula (X).

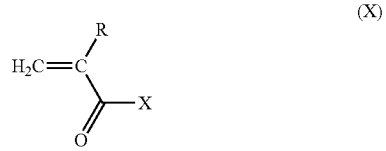

(In formula (X), R represents a hydrogen atom or a methyl group, and X represents a group including a structure similar to a biological component.)

The acrylic acid or methacrylic acid represented by the above-described formula (X) may be obtained by, for example, glucosyloxyethylesterification, trimethylaminoethoxyphosphoethylesterification, or amidation with an amino acid (for example, lysine) of acrylic acid or methacrylic acid, but the method is not limited thereto.

There is performed addition polymerization of one or two or more kinds of the produced vinyl monomers in each of which a structure similar to a biological component is inserted (preferably, acrylic acids or methacrylic acids each represented by the above-described formula (X)). In fact, only vinyl monomers in each of which a structure similar to a biological component is inserted may be polymerized, but if necessary, the monomers may be copolymerized together with any other vinyl monomer (a vinyl monomer in which a structure similar to a biological component is not inserted). In fact, examples of the other vinyl monomer include, but not limited to, one or two or more kinds of monomers selected from an acrylic acid, methacrylic acid, alkyl acrylate, and alkyl methacrylate.

The (co)polymer to be included in the external skin agent of the present invention may be a polymer prepared by regular polymerization (such as block copolymerization) of a vinyl monomer in which a structure similar to a biological component is inserted with any other vinyl monomer, but preferably is a polymer obtained by random copolymerization.

Meanwhile, the (co)polymer to be included in the external skin agent of the present invention preferably includes a vinyl monomer in which a structure similar to a biological component is inserted (A) and any other vinyl monomer (B) at a unit ratio of (A):(B)=100:0 to 5:95.

The weight average molecular weight of the (co)polymer that is included in the external skin agent of the present invention may be $1 \times 10^4$ to $1 \times 10^6$, but it is not particularly limited.

The polymerization reaction conditions of the above-described polymerization may be the same conditions as those of a general polymerization reaction of an acrylic acid or the like. For example, the reaction may be performed in a solution or dispersion and may be performed using a polymerization initiator. An example of the polymerization initiator includes azobisisobutyronitrile.

The (co)polymer that is included in the external skin agent of the present invention may be one of the known (co)polymers or commercially available (co)polymers. Some of them are used as materials for skin preparations for external use. The external skin agent of the present invention may include any one of those commercially available (co)polymers.

Preferable examples of the commercially available (co) polymers include polyglucosyloxyethyl methacrylate (manufactured by Nippon Fine Chemical, "p-GEMA-s"), polymethacryloyl lysine (manufactured by Gifu Shellac, "PM lysine"), polymethacryloyloxyethyl phosphorylcholine (manufactured by NOF Corporation, "Lipidurer-C"), methacryloyloxyethyl phosphorylcholine-butyl methacrylate copolymer (manufactured by NOF Corporation, "Lipidurer-PMB"), and methacryloyloxyethyl phosphorylcholine-stearyl methacrylate copolymer (manufactured by NOF Corporation, "Lipidurer-S"). More preferable one is "Lipidurer-C".

<3. External Skin Agent of the Present Invention>

The external skin agent of the present invention includes the above-described modified clay and (co)polymer as essential ingredients.

The external skin agent of the present invention may include a single kind of the above-described modified clay or may include two or more kinds of the above-described modified clays in combination. The total content of the above-described modified clay in the external skin agent of the present invention is preferably 0.1 to 5% by mass, more preferably 0.5 to 3% by mass with respect to the total amount of the external skin agent.

If the content is significantly lower than the lower limit of the above-described content, the stabilizing effect of the above-described modified clay on an emulsification and emulsified product are not expressed in some cases. If the content is significantly higher than the upper limit of the above-described content, hardening occurs owing to gelatinization, which adversely causes water release or the like, and the stability of an external skin agent is impaired in some cases.

The modified clay that is included in the external skin agent of the present invention is preferably dispersed in an external skin agent.

The external skin agent of the present invention may include a single kind of the above-described (co)polymer or may include two or more kinds of the above-described (co)polymers in combination. The total content of the above-described (co)polymer in the external skin agent of the present invention is preferably 0.1 to 10% by mass, more preferably 1 to 5% by mass with respect to the total amount of the external skin agent.

If the content is significantly lower than the lower limit of the above-described content, the effect to improve skin inflammation is not sufficiently exerted in some cases even if the external skin agent is applied. If the content is significantly higher than the upper limit of the above-described content, although the above-described effect has peaked, the stability of the system is impaired in some cases.

The (co)polymer that is included in the external skin agent of the present invention is preferably dissolved or dispersed in an external skin agent.

As described above, the external skin agent of the present invention preferably includes a silicone in addition to the above-described essential ingredients. The silicone to be included may be used without particular limitations as long as it is generally used in an external skin agent. Preferable examples thereof include dimethicone, phenylmethicone, cyclomethicone, and alkylenoxide methylsiloxane copolymer.

In particular, the external skin agent of the present invention preferably includes at least three kinds of silicones including a volatile silicone, a low-viscosity silicone, and a middle-viscosity silicone.

Herein, the volatile silicone means a silicone having a boiling point of 200° C. or lower at 1 atm. Suitable examples thereof include: cyclomethicones such as dimethicone cyclic pentamer, dimethicone cyclic tetramer, and dimethicone cyclic trimer; and a dimethicone having a viscosity of 5 mPascal·sec or less at 1 atm and 20° C.

The low-viscosity silicone means a silicone having a viscosity of 10 to 1,000 mPascal·sec, more preferably 10 to 500 mPascal·sec at 1 atm and 20° C.

The middle-viscosity silicone means a silicone having a viscosity of 1,000 to 100,000 mPascal·sec, more preferably 5,000 to 70,000 mPascal·sec at 1 atm and 20° C.

When at least three kinds of silicones including a volatile silicone, a low-viscosity silicone, and a middle-viscosity silicone are included in the external skin agent of the present invention, a friction in applying the external skin agent to skin is reduced, so that irritation caused by the friction to skin is reduced. Moreover, when the three kinds of silicones are included, the water resistance of a coating formed by applying the external skin agent is improved, so that sticky feeling characteristic of oiliness is reduced.

The total content of a silicone in the external skin agent of the present invention is preferably 20 to 40% by mass, more preferably 25 to 35% by mass with respect to the total amount of the external skin agent. This is because if the silicone content is significantly high, usability is impaired in some cases owing to stickiness, while if the content is significantly low, the above-described effect is not exerted in some cases.

Further, the external skin agent of the present invention preferably includes a volatile silicone, a low-viscosity silicone, and a middle-viscosity silicone at concentrations of 0.1 to 3% by mass, 15 to 25% by mass, and 5 to 10% by mass, respectively, with respect to the total amount of the external skin agent.

The anti-inflammatory effect of the external skin agent of the present invention is not exactly dependent on the skin's moisture-retention such as inhibition of the amount of transepidermal water loss. However, impartation of water resistance to skin has an advantage in that penetration of a water-soluble pro-inflammatory ingredient to skin may be prevented. Therefore, as described above, the external skin agent of the present invention preferably includes a silicone.

Meanwhile, the external skin agent of the present invention may include an alkylenoxide methylsiloxane copolymer as a surfactant.

Examples of the alkylenoxide methylsiloxane copolymer include polyoxyethylene methylsiloxane copolymer, and polyoxypropylene methylsiloxane copolymer. The alkylenoxide methylsiloxane copolymer may partially have a crosslinking structure.

Some alkylenoxide methylsiloxane copolymer are commercially available, so that any one of such alkylenoxide methylsiloxane copolymer may be purchased and included in the external skin agent of the present invention. Preferable examples thereof include: a polyoxyethylene adduct such as "Silicone KF-6011", "Silicone KF-6013", "Silicone KF-6014", "Silicone KF-6015", "Silicone KF-6016", "Silicone KF-6017", or "Silicone KF-6018"; and a polyoxyethylene-polyoxypropylene adduct such as "Silicone KF-6012" (all products are manufactured by Shin-Etsu Chemical Co., Ltd.). Of those, "Silicone KF-6017" is preferably exemplified.

The external skin agent of the present invention may include one kind of alkylenoxide methylsiloxane copolymer or may include two or more kinds of alkylenoxide methylsiloxane copolymers in combination. The alkylenoxide methylsiloxane copolymer has an effect to stabilize an emulsion structure of the external skin agent of the present invention as well as the above-described properties as a silicone.

The alkylenoxide methylsiloxane copolymer content in the external skin agent of the present invention is preferably 0.1 to 10% by mass, more preferably 1 to 6% by mass with respect to the total amount of the external skin agent. If the content is significantly low, the above-described effect to stabilize the emulsion structure is not sufficiently exerted in some cases, while if the content is significantly high, the stability is impaired in some cases.

The external skin agent of the present invention preferably further includes the above-described alkylenoxide methylsiloxane copolymer in addition to the above-described volatile silicone, low-viscosity silicone, and middle-viscosity silicone that are dimethicones and/or phenyl methicones.

As described above, the external skin agent of the present invention preferably includes an ingredient having an anti-inflammatory effect. When the ingredient having an anti-inflammatory effect is included, the anti-inflammatory effect of the external skin agent of the present invention may further be improved.

Preferable examples of the ingredients having an anti-inflammatory effect include one or two or more kinds selected from the group consisting of plant alcohol extracts (inclusive of alcohol extract of Compositae *Arctium lappa*, alcohol extract of Arallaceae *Panax Notoginseng*, alcohol extract of Betulaceae *Betula maximowicziana*, alcohol extract of Leguminosae *Sophora flavescens*, alcohol extract of Lamiaceae *Salvia officinalis*, alcohol extract of Juglandaceae *Engelhardtia chrysolepis*, and alcohol extract of Compositae *Achillea millefolium*, and alcohol extract of Lamiaceae *Rosmarinus officinalis*), glycyrrhizinic acid and/or a salt thereof, glycyrrhetinic acid esters (such as stearyl glycyrrhetinate), ursolic acid and/or a salt thereof, ursolic acid ester, a glycoside of plant steroid (phytosterol), indomethacin, ketoprofen, ketotifen, bufexamac, dexamethasone, prednisolone, beclomethasone, betamethasone, hydrocortisol, tacrolimus, and ibuprofen.

The above-described plant alcohol extract is an ingredient obtained by an extraction treatment of a plant with an alcohol that is an extraction solvent. Preferable examples of the alcohol that is an extraction solvent include: monovalent alcohols such as ethanol and isopropanol; and polyvalent alcohols such as 1,3-butanediol, propylene glycol, and glycerin.

The above-described plant alcohol extract may be included in the external skin agent of the present invention together with an extraction solvent used for extraction or may be included therein after removal (for example, removal by distillation) of the extraction solvent. In the case that the extraction solvent has volatility, the extract is preferably included after removal of the extraction solvent, while in the case of the extraction solvent has no volatility like a polyvalent alcohol or the like, the extract is preferably included together with the extraction solvent.

The total content of an anti-inflammatory ingredient in the external skin agent of the present invention is preferably 0.01 to 5% by mass, more preferably 0.02 to 1% by mass.

As described below, the dosage form of the external skin agent of the present invention is preferably a form of an emulsion. In the case that the external skin agent of the present invention is in the form of an emulsion, it preferably includes a sucrose fatty acid ester as an emulsifier. Preferable examples of the sucrose fatty acid ester include sucrose monolaurate, sucrose monostearate, sucrose dilaurate, and sucrose distearate. Of those sucrose monolaurate is particularly preferable.

In general, the external skin agent in the form of an emulsion includes a nonionic surfactant (in particular, polyoxyethylene-added nonionic surfactant) for stabilizing its emulsification state. However, the nonionic surfactant is strongly irritant to skin.

Meanwhile, the external skin agent of the present invention is characterized by being used for alleviating skin inflammation, so that it is preferable that irritation to inflammation be low. Therefore, even if the external skin agent of the present invention is in the form of an emulsion, it is preferable that the content of a nonionic surfactant (in particular, polyoxyethylene-added nonionic surfactant) below. The above-described sucrose fatty acid ester may stabilize emulsification of the external skin agent of the present invention, so that it is possible that the polyoxyethylene-added nonionic surfactant content is reduced or is substantially zero.

As described above, from the viewpoint of restricting the content of a nonionic surfactant (in particular, polyoxyethylene-added nonionic surfactant), the external skin agent of the present invention preferably includes a sucrose fatty acid ester at a concentration of 0.1 to 2% by mass, more preferably 0.2 to 1% by mass.

Meanwhile, the polyoxyethylene-added nonionic surfactant content in the external skin agent of the present invention is preferably restricted to lower-level, and the content is 1% by mass or less, more preferably 0.5% by mass or less, particularly preferably zero.

The external skin agent of the present invention can contain any ingredient other than the above ingredients used generally in an external skin agent. Examples of the ingredient used generally include oils/waxes, hydrocarbons, higher fatty acids, higher alcohols, oil solutions of synthetic ester oils, surfactants, polyvalent alcohols, moisture components, thickeners, fine particles, inorganic pigments, pearl agents, organic dyes, organic fine particles, ultraviolet absorbents, lower alcohols, and vitamins.

Examples of the oils/waxes include macadamia nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax.

Examples of the hydrocarbons include liquid paraffin, squalane, pristane, ozokerite, paraffin, ceresin, vaseline, and microcrystalline wax.

Examples of the higher fatty acids include oleic acid, isostearic acid, lauric acid, myristic acid, palmitic acid, stearic acid, behenic acid, and undecylenic acid.

Examples of the higher alcohols include cetyl alcohol, stearyl alcohol, isostearyl alcohol, behenyl alcohol, octyldodecanol, myristyl alcohol, and cetostearyl alcohol.

Examples of the oil solutions of synthetic ester oils include synthetic ester oils such as cetyl isooctanoate, isopropylmyristate, hexyldecyl isostearate, diisopropyl adipate, di-2-ethylhexyl sebacate, cetyl lactate, diisostearyl malate, ethylene glycol di-2-ethyl hexanoate, neopentylglycol dicaprate, di-2-heptyl undecanoic acid glyceride, tri-2-ethylhexanoic acid glyceride, trimethylolpropane tri-2-ethylhexanoate, trimethylolpropane triisostearate, and pentaerythrit tetra-2-ethylhexanoate.

Examples of the surfactants include anionic surfactants, cationic surfactants, amphoteric surfactants, and nonionic surfactants.

Examples of the anionic surfactants include fatty acid soaps (such as sodium laurate and sodium palmitate), potassium laurylsulfate, and triethanolamine alkylsulfate ether.

Examples of the cationic surfactants include trimethyl ammonium stearyl chloride, benzalkonium chloride, and laurylamine oxide.

Examples of the amphoteric surfactants include imidazoline-based amphoteric surfactants (such as a 2-cocoyl-2-imidazolinium hydroxide-1-carboxyethyloxy-2-sodium salt), betaine-based surfactants (such as alkyl betaine, amide betaine, and sulfo betaine), and acylmethyl taurine.

Examples of the nonionic surfactants include sorbitan fatty acid esters (such as sorbitan monostearate and sorbitan sesquioleate), glycerin fatty acids (such as glycerin monostearate), propyleneglycol fatty acid esters (such as propyleneglycol monostearate), cured castor oil derivatives, glycerol alkylether, POE sorbitan fatty acid esters (such as POE sorbitan monooleate and polyoxyethylene sorbitan monostearate), POE sorbitol fatty acid esters (such as POE-sorbitol monolaurate), POE glycerol fatty acid esters (such as POE-glyceryl monoisostearate), POE fatty acid esters (such as polyethyleneglycol monooleate and POE distearate), POE alkyl ethers (such as POE2-octyldodecyl ether), POE alkylphenyl ethers (such as POE nonylphenylether), pluronic types, POE/POP alkyl ethers (such as POE/POP2-decyltetradecyl ether), tetronic types, POE castor oil/cured castor oil derivatives (such as POE castor oil and POE cured castor oil), sucrose fatty acid ester, and alkyl glycoside.

Examples of the polyvalent alcohols include polyethylene glycol, glycerin, 1,3-butylene glycol, erythritol, sorbitol, xylitol, maltitol, propylene glycol, dipropylene glycol, diglycerin, isoprene glycol, 1,2-pentanediol, 2,4-hexylene glycol, 1,2-hexanediol, and 1,2-octanediol.

Examples of the moisture components include sodium pyrrolidone carboxylate, lactate, and sodium lactate.

Examples of the thickeners include guar gum, quince seed, carageenan, galactan, gum arabic, pectin, mannan, starch, xanthan gum, curdlan, methyl cellulose, hydroxyethyl cellulose, carboxymethyl cellulose, methylhydroxypropyl cellulose, chondroitin sulfate, dermatan sulfate, glycogen, heparan sulfate, hyaluronic acid, sodium hyaluronate, tragacanth gum, keratan sulfate, chondroitin, mucoitin sulfate, hydroxyethyl guar gum, carboxymethyl guar gum, dextran, keratosulfate, locust bean gum, succinoglucan, calonic acid, chitin, chitosan, carboxymethyl chitin, agar, polyvinyl alcohol, polyvinyl pyrrolidone, a carboxyvinyl polymer, sodium polyacrylate, polyethylene glycol, and bentonite.

Examples of the fine particles include mica, talc, kaolin, synthetic mica, calcium carbonate, magnesium carbonate, silicic acid anhydride (silica), aluminum oxide and barium sulfate, whose surfaces may be treated.

Examples of the inorganic pigments include red iron oxide, yellow iron oxide, black iron oxide, cobalt oxide, ultramarine blue, iron blue, titanium oxide and zinc oxide, whose surfaces may be treated.

Examples of the pearl agents include mica titanium, fish scale foil and bismuth oxychloride, whose surfaces may be treated.

Examples of the organic dyes include Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201 and Red No. 204, which may be laked.

Examples of the organic fine particles include polyethylene powder, poly(methyl methacrylate), nylon powder, and organopolysiloxane elastomer.

Examples of the ultraviolet absorbents include a p-aminobenzoate-based ultraviolet absorbent, an anthranilate-based ultraviolet absorbent, a salicylate-based ultraviolet absorbent, a cinnamate-based ultraviolet absorbent, a benzophenone-based ultraviolet absorbent, a sugar-based ultraviolet absorbent, 2-(2'-hydroxy-5'-t-octylphenyl)benzotriazole, and 4-methoxy-4'-t-butyldibenzoylmethane.

Examples of the lower alcohols include ethanol, isopropanol, and phenoxyethanol.

Examples of the vitamins include: vitamin A or derivatives thereof; vitamin B types such as vitamin B6 hydrochloride, vitamin B6 tripalmitate, vitamin B6 dioctanoate, vitamin B2 or derivatives thereof, vitamin B12, and vitamin B15 or derivatives thereof; vitamin E types such as α-tocopherol, β-tocopherol, γ-tocopherol, and vitamin E acetate; vitamin D types; vitamin H; pantothenic acid; pantethine; and pyrroloquinoline quinone.

The dosage form of the external skin agent of the present invention is not particularly limited, but it is preferably a form of an emulsion, more preferably a form of a water-in-oil emulsion. Of those forms of water-in-oil emulsions, preferable is a form of a high internal phase water-in-oil emulsion containing 50% by mass or more of an internal phase. This is because when the external skin agent of the present invention is in the form of an emulsion (preferably, in the form of a water-in-oil emulsion), the preparation may enhance skin's moisture-retention ability and may significantly improve skin's barrier function.

In the case that the external skin agent of the present invention is a form of an emulsion, it preferably includes a sucrose fatty acid ester as an emulsifier as described above.

The external skin agent of the present invention may be used for treating or preventing skin inflammation, but it is preferably used for preventing onset of skin inflammation (for preventing inflammation). More preferably, the preparation is used for preventing inflammation caused by invading a pro-inflammatory substance or the like in corium owing to lowering of skin's barrier function. Therefore, the external skin agent of the present invention may have an indication stating the fact that the preparation has an anti-inflammatory effect or inflammatory-preventive effect (for example, the fact may be indicated in its package).

Inflammation to be treated or prevented by the external skin agent of the present invention is preferably inflammation caused by atopic dermatitis. The external skin agent of the present invention enhances skin's moisture-retention ability and skin's barrier function and exerts an effect to inhibit onset of atopic skin inflammation (inflammation-preventive effect). Moreover, the preparation may prevent the recurrence of atopic dermatitis due to lowered skin's barrier function.

This is because the external skin agent of the present invention has multiple functions to: 1) inhibit increase in transepidermal water loss caused by inflammation; 2) inhibit migration of an inflammation factor induced by increase in transepidermal water loss; and 3) prevent invasion of a pro-inflammatory ingredient caused by lowered skin's barrier function. The fact is described also in Examples below.

The external skin agent of the present invention is preferably externally administered to skin. The external administration to skin includes percutaneous administration, which includes application to skin as a topical cream and application as an adhesive skin patch.

The external skin agent of the present invention may be applied to any composition to be externally administered to skin. Preferable examples of the composition to be externally administered to skin include skin drugs for external use, cosmetics (including quasi drugs), and skin goods for external use. Particularly preferable are cosmetics. In particular, the external skin agent of the present invention is preferably applied to a quasi drug. The quasi drug refers to a quasi drug defined by the Pharmaceutical Affairs Law.

In the case that the external skin agent of the present invention is a quasi drug, an anti-inflammatory agent is incorporated in the preparation as an active ingredient, to thereby prepare a quasi drug appealing to buyers for its anti-inflammatory effect. In this case, "appealing to buyers for its anti-inflammatory effect" includes showing the fact that the preparation is a quasi drug having an anti-inflammatory effect in its package.

The external skin agent of the present invention may be produced in the same way as a method of producing a general external skin agent depending on its dosage form except that the above-described modified clay and (co)polymer are included.

EXAMPLES

Hereinafter, the present invention will be described in more detail with reference to examples, but it will be obvious that the present invention is not limited to the examples.

Example 1

According to the prescription shown in Table 1 below, the external skin agent of the present invention was prepared.

Ingredient III was dispersed in Ingredient I heated to 80° C. While Ingredient I including dispersed Ingredient III was stirred, Ingredient II heated to 80° C. was gradually added thereto to emulsify the mixture. The resultant emulsified product was cooled with stirring, to thereby yield a milky lotion in the form of a water-in-oil emulsion. Hereinafter, the lotion will be referred to as "Cream A".

Meanwhile, according to the prescription shown in Tables 2 and 3 below, the external skin agent of the present invention was prepared.

Ingredients I, III, and IV were heated to 75° C., and the mixture was solubilized by stirring. Ingredient II was added to Ingredient I heated to 75° C., and the mixture was kneaded. Then, Ingredient III heated to 75° C. was added thereto, followed by dilution. The resultant diluted product was gradually added with Ingredient IV heated to 75° C. with stirring to emulsify the mixture. The resultant emulsified product was cooled with stirring, to thereby yield a milky lotion in the form of a water-in-oil emulsion. Hereinafter, the lotions will be referred to as "Cream A-2" and "Cream B".

TABLE 1

| Cream A | |
|---|---|
| (Ingredient I) | |
| Dimethicone (10 mPascal · sec) | 8% by mass |
| Dimethicone (50,000 mPascal · sec) | 1% by mass |
| Cyclomethicone (Pentamer) | 22% by mass |
| Sucrose monostearate | 0.5% by mass |
| Squalane | 2% by mass |
| Stearyl glycyrrhetinate | 0.05% by mass |
| alkylenoxide methylsiloxane copolymer (Silicone KF-6017) | 4% by mass |
| (Ingredient II) | |
| Polyethyleneglycol 400 | 1% by mass |
| 1,3-Butanediol | 1% by mass |
| Glycerin | 12% by mass |
| Phenoxyethanol | 0.5% by mass |
| Lipidurer-C | 2% by mass |
| Water | 43.95% by mass |
| (Ingredient III) | |
| Bentone-38V | 2% by mass |

TABLE 2

| Cream A-2 | |
|---|---|
| (Ingredient I) | |
| Glycerin | 11.8% by mass |
| Polyethylene glycol 750 | 1% by mass |
| 1,3-Butanediol | 0.4% by mass |
| Phenoxyethanol | 0.5% by mass |
| Methyl paraben | 0.3% by mass |
| Butyl paraben | 0.1% by mass |
| (Ingredient II) | |
| Bentone-38V | 2% by mass |
| (Ingredient III) | |
| Dimethicone (10 mPascal · sec) | 8% by mass |
| Dimethicone (50,000 mPascal · sec) | 1% by mass |
| Cyclomethicone (Pentamer) | 22% by mass |
| Sucrose monostearate | 0.5% by mass |
| Squalane | 2% by mass |
| Sorbitan isostearate | 2.5% by mass |
| Sucrose stearate | 0.3% by mass |
| Sucrose palmitate | 0.2% by mass |
| δ-tocopherol | 0.02% by mass |
| (Ingredient IV) | |
| Polymethacryloyloxyethyl phosphorylcholine | 0.2% by mass |
| Dipotassium glycyrrhizinate | 0.05% by mass |
| Water | 47.13% by mass |

TABLE 3

| Cream B | |
|---|---|
| (Ingredient I) | |
| Glycerin | 11.8% by mass |
| Polyethylene glycol 750 | 1% by mass |
| 1,3-Butanediol | 0.4% by mass |
| Phenoxyethanol | 0.5% by mass |
| Methyl paraben | 0.3% by mass |
| Butyl paraben | 0.1% by mass |
| (Ingredient II) | |
| Bentone-38V | 2% by mass |
| (Ingredient III) | |
| Squalane | 33% by mass |
| Sorbitan isostearate | 2.5% by mass |
| Sucrose stearate | 0.3% by mass |
| Sucrose palmitate | 0.2% by mass |
| δ-tocopherol | 0.02% by mass |
| (Ingredient IV) | |
| Polymethacryloyloxyethyl phosphorylcholine | 0.2% by mass |
| Dipotassium glycyrrhizinate | 0.05% by mass |
| Water | 47.63% by mass |

Test Example 1-1

Preventive Effect on Dermatitis of NC/Nga Mouse

As test animals, 10 NC/Nga male mice (6 to 7-week) each having a body weight of about 30 g were used for one sample (Cream A, white petrolatum, and no treatment). NC/Nga mice raised under conventional conditions developed skin lesions spontaneously with diagnostic characteristics of a high concentration of total immunoglobulin E in the plasma and invasion of inflammatory cells into the lesions. (see Documents 1, 2, and 3 below).

The above-described Cream A (50 mg/mouse), or white petrolatum (50 mg/mouse) was applied to the rostral back skin of each mouse 8 weeks at a frequency of 5 times/week. After 8 weeks, the skin symptoms were observed in the rostral backs of the mice of each group, and the observed skin symptoms were classified into 7 levels to evaluate the preventive effects on exacerbation of the inflammations with time. The observed skin symptoms were judged as 0 to 6 points according to the criteria shown in Table 4 below.

Test Example 1-2

Preventive Effect on Dermatitis of NC/Nga Mouse

As test animals, 10 NC/Nga male mice (6 to 7-week old) each having a body weight of about 30 g were used for one sample (Cream A-2, Cream B, and no treatment).

The above-described Cream A-2 (50 mg/mouse), or Cream B (50 mg/mouse) was applied to the rostral back skin of each mouse 8 weeks at a frequency of 5 times/week. After 8 weeks, the skin symptoms were observed in the rostral backs of the mice of each group, and the observed skin symptoms were classified into 7 levels to evaluate the preventive effects on exacerbation of the inflammations with time. The observed skin symptoms were judged as 0 to 6 points according to the criteria shown in Table 4 below.

Document 1: Kondo, K., Nagami, T., Teramoto, S., 1964. Differences in haematopoietic death among inbred strains of mice. In Bond, S. V., Sugahara, T. (Eds.), Comparative Cellular and Species Radiosensitivity. Tokyo, Igakushoin. 20.

Document 2: Matsuda, H., Watanabe, N., Geba, G. P., Sperl, J., Tsudzuki, M., Hiroi, J., Matsumoto, M., Ushio, J., Saito, S., Askenase, P. W., Ra, C., 1997. Development of atopic dermatitis-like skin lesion with IgE hyperproduction in NC/Nga mice. Int. Immunol. 9, 461-466.

Document 3: Suto, H., Matsuda, H., Mitsuishi, K., Hira, K., Uchida, T., Unno, T., Ogawa, H., Ra, C., 1999. NC/Nga mice: a mouse model for atopic dermatitis. Int. Arch. Allergy Immunol. 120 (suppl. 1), 70-75

TABLE 4

| Dermatitis Score | Symptoms | criteria for evaluation |
| --- | --- | --- |
| 0 | No symptom | No eruption |
| 1 | Mild | No change in fur, slight scaling |
| 2 | | No change in fur, scaling, inflammation accompanied by slight bleeding |
| 3 | Moderate | Change in fur, inflammation accompanied by slight bleeding |
| 4 | | Change in fur, inflammation accompanied by extensive bleeding |
| 5 | Severe | Significant change in fur, inflammation accompanied by severe bleeding |
| 6 | | Significant change in fur, inflammation accompanied by extensive severe bleeding |

For each sample (Test Example 1-1: Cream A, white petrolatum, and no treatment) (Test Example 1-2: Cream A-2, Cream B, and no treatment), the mean of the resultant judged scores was calculated. The results are shown in FIG. 1 (Test Example 1-1) and FIG. 2 (Test Example 1-2).

As shown in FIG. 1, the judged result for NC/Nga mice of the no treatment group after breeding over 8 weeks was found to be 3.3±0.4. White petrolatum demonstrated a tendency to inhibit onset of dermatitis, but there was no significant difference compared to no treatment. On the other hand, Cream A was found to have an effect to significantly inhibit onset of dermatitis. The results revealed that Cream A effectively prevents atopic dermatitis.

Figure 2:
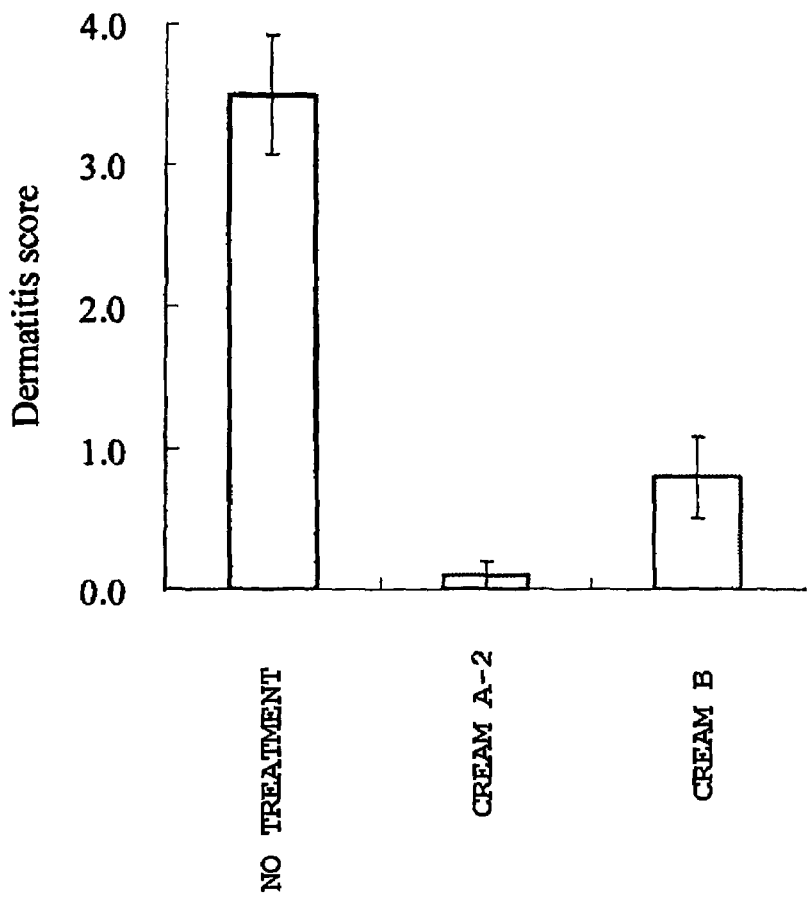
FIG. 2 is a graph showing the results of Test Example 1-2.

Meanwhile, as shown in FIG. 2, comparison of Cream A-2 and Cream B revealed that the effect to prevent atopic dermatitis is further enhanced depending on the silicone proportion.

Test Example 2

Determination of Water-Loss-Inhibiting Effect

As described below, a water-loss-inhibiting test was performed using an acrylic cup.

A filter paper coated with keratin powder was set on an acrylic cup. 0.2 g of a sample (Cream A or petrolatum) was applied to the filter paper. The cup was allowed to stand at a temperature of 30° C. and a humidity of 30% for 24 hours. Thereafter, the water loss was determined. The determination results are shown in Table 5 below.

TABLE 5

Water-loss-inhibiting effect

| Sample | Water loss |
| --- | --- |
| Cream A | 0.8717 g |
| Petrolatum | 0.03612 g |

As shown in Table 5, both Cream A and petrolatum were found to have water-loss-inhibiting effects, but the degree of the water-loss-inhibiting effect of Cream A was found to be lower than that of petrolatum. It is generally believed that atopic dermatitis is alleviated by inhibiting water loss. Although Cream A has a lower water-loss-inhibiting effect than that of petrolatum, it has an excellent effect to prevent atopic dermatitis as shown in Test Example 1-1. The results revealed that the external skin agent of the present invention prevents atopic dermatitis by conventionally unknown action mechanism.

Test Example 3

Determination of Skin Function Improving Effect

Cream A in Example 1 was used to investigate the skin function improving effect by a combination of organically modified clay and a polymer having a structure similar to biological component using the transepidermal water loss (TEWL) as an indicator. That is, the whole forearms of subjects (n=2) were washed well, and then three portions each having a size of 2 cm×4 cm were set in the inner portion of the forearm. Then, TEWLs were determined (TEWL1) with a tewameter (manufactured by Integral, Inc.), and it was confirmed that there were no differences between the individual subjects and between the portions of each subject. Thereafter, stripping was performed 15 times with an adhesive tape to prepare artificial skin roughness models. After stripping, the forearms were allowed to stand for 30 minutes to wait for disappearance of the effects of the stripping, and TEWLs were determined (TEWL2) to reconfirm that there was no difference between the respective portions of each subject. Subsequently, 50 μg of a sample was immediately administered, and the forearms were allowed to stand for 1 hour and washed well. Then, the forearms were allowed to stand for 10 minutes, and TEWLs were determined (TEWL3). From the resultant TEWLs 1 to 3, TEWL inhibition ratio was calculated according to the following formula [1]. Meanwhile, in addition to Cream A in Example 1, there were used, as samples, a product prepared by substituting "Lipidurer-C" in Cream A in Example 1 by water (Comparative Example 1) and a product prepared by substituting "Bentone-38V" in Cream A by water (Comparative Example 2). The results are shown in Table 6. The results revealed that a combination of organically modified clay and a polymer having a structure similar to a biological component in the external skin agent of the present invention generated a skin function improving effect. That is, it was found that when An external skin agent including organically modified clay and a polymer having a structure similar to a biological component was administered, reconstruction of a barrier layer on skin was rapidly promoted, resulting in improved skin functions. Such effects probably contribute to alleviation of atopic dermatitis.

$$\text{TEWL inhibition ratio (\%)} = (1-(TEWL3-TEWL1)/(TEWL2-TEWL1)) \times 100 \quad [1]$$

TABLE 6

| Samples | TEWL inhibition ratio (%)* |
| --- | --- |
| Cream A | 70.9 |
| Comparative example 1 | 53.1 |
| Comparative example 2 | 16.8 |

*TEWL inhibition ratio (%) is represented as a mean of the subjects (n = 2)

Examples 2 to 5

In the same way as Example 1, the skin preparations for external use of the present invention were prepared according to the prescriptions shown in Tables 7 and 8 below. The skin preparations for external use prepared in Examples 2 to 5 may be used as quasi drugs. The prepared quasi drugs were administered to the damaged skin of a volunteer (n=1), and irritation-feeling tests were performed to evaluate the preparations. Specifically, a sample (40 μl) was administered to an inner portion of a forearm (1×2 cm) that had been subjected to stripping with a sealing tape three times, and it was judged whether irritation was felt at the time when the portion was frictioned five times.

None of the quasi drugs 2 to 5 induced irritation feeling. The results revealed that all the (co)polymers each having a side chain including a structure similar to a biological component as shown in Table 8 may be appropriately applied to the skin preparations for external use of the present invention.

TABLE 7

| Prescription | |
|---|---|
| (Ingredient I) | |
| Dimethicone (10 mPascal · sec) | 8% by mass |
| Dimethicone (50,000 mPascal · sec) | 1% by mass |
| Cyclomethicone (Pentamer) | 22% by mass |
| Sucrose monostearate | 0.5% by mass |
| Squalane | 2% by mass |
| Stearyl glycyrrhetinate | 0.05% by mass |
| alkylenoxide methylsiloxane copolymer (Silicon KF-6017) | 4% by mass |
| (Ingredient II) | |
| Polyethyleneglycol 400 | 1% by mass |
| 1,3-Butanediol | 1% by mass |
| Glycerin | 12% by mass |
| Phenoxyethanol | 0.5% by mass |
| Polymer described in Table 8 | 2% by mass |
| Water | 43.95% by mass |
| (Ingredient III) | |
| Bentone-38V | 2% by mass |

TABLE 8

| Example | Polymer having structure similar to biological component |
|---|---|
| Example 2 | p-GEMA-s |
| Example 3 | Lipidurer-PMB |
| Example 4 | Lipidurer-S |
| Example 5 | PM lysine |

Examples 6 and 7

In the same way as Example 1, the skin preparations for external use of the present invention were produced according to the prescriptions shown in Tables 9 and 10 below. The skin preparations for external use prepared in Examples 6 and 7 may be used as quasi drugs. The prepared quasi drugs were administered to the damaged skin of a volunteer (n=1) in the same way as Example 2, and irritation-feeling tests were performed to evaluate the preparations. None of the samples induced irritation feeling.

TABLE 9

| Prescription | |
|---|---|
| (Ingredient I) | |
| Dimethicone (10 mPascal · sec) | 8% by mass |
| Dimethicone (50,000 mPascal · sec) | 1% by mass |
| Cyclomethicone (Pentamer) | 22% by mass |
| Sucrose monostearate | 0.5% by mass |
| Squalane | 2% by mass |
| Stearyl glycyrrhetinate | 0.05% by mass |
| alkylenoxide methylsiloxane copolymer (Silicon KF-6017) | 4% by mass |
| (Ingredient II) | |
| Polyethyleneglycol 400 | 1% by mass |
| 1,3-Butanediol | 1% by mass |
| Glycerin | 12% by mass |
| Phenoxyethanol | 0.5% by mass |
| Lipidurer-C | 2% by mass |
| Water | 43.95% by mass |
| (Ingredient III) | |
| Modified clay described in Table 10 | 2% by mass |

TABLE 10

| Example | Modified clay |
|---|---|
| Example 6 | Organically modified kaolinite (Production Example 1) |
| Example 7 | Organically modified montmorillonite (Production Example 2) |

Examples 8 to 18

In the same way as Example 1, the skin preparations for external use of the present invention were produced according to the prescriptions shown in Tables 11 and 12 below. The skin preparations for external use prepared in Examples 8 to 18 may be used as quasi drugs. The prepared quasi drugs were administered to the damaged skin of a volunteer (n=1) in the same way as Example 2, and irritation-feeling tests were performed to evaluate the preparations. None of the samples induced irritation feeling.

TABLE 11

| Prescription | |
|---|---|
| (Ingredient I) | |
| Dimethicone (10 mPascal · sec) | 8% by mass |
| Dimethicone (50,000 mPascal · sec) | 1% by mass |
| Cyclomethicone (Pentamer) | 22% by mass |
| Sucrose monostearate | 0.5% by mass |
| Squalane | 2% by mass |
| Stearyl glycyrrhetinate | 0.05% by mass |
| alkylenoxide methylsiloxane copolymer (Silicon KF-6017) | 4% by mass |
| (Ingredient II) | |
| Anti-inflammatory ingredient described in Table 12 | 0.05% by mass |
| Polyethyleneglycol 400 | 1% by mass |
| 1,3-Butanediol | 1% by mass |
| Glycerin | 12% by mass |
| Phenoxyethanol | 0.5% by mass |
| Lipidurer-C | 2% by mass |
| Water | 43.9% by mass |
| (Ingredient III) | |
| Bentone-38V | 2% by mass |

TABLE 12

| Example | Anti-inflammatory ingredients |
| --- | --- |
| Example 8 | Solvent-removed product of ethanol extract of Compositae *Arctium lappa* |
| Example 9 | Solvent-removed product of ethanol extract of Araliaceae *Panax Notoginseng* |
| Example 10 | Solvent-removed product of ethanol extract of Betulaceae *Betula maximowicziana* |
| Example 11 | 1,3-Butanediol extract of Leguminosae *Sophora flavescens* |
| Example 12 | 1,3-Butanediol extract of Lamiaceae *Salvia officinalis* |
| Example 13 | Solvent-removed product of ethanol extract of Juglandaceae *Engelhardtia chrysolepis* |
| Example 14 | Solvent-removed product of ethanol extract of Compositae *Achillea millefolium* |
| Example 15 | 1,3-Butanediol extract of Lamiaceae *Rosmarinus officinalis* |
| Example 16 | Sodium ursolate |
| Example 17 | Benzyl ursolate |
| Example 18 | Sitosterol-α-glucoside |

Examples 19 to 24

In the same way as Example 1, the skin preparations for external use of the present invention were produced according to the prescriptions shown in Tables 13 and 14 below. The skin preparations for external use prepared in Examples 19 to 24 may be used as anti-inflammatory skin external medicines. The prepared anti-inflammatory skin external medicines were administered to the damaged skin of a volunteer (n=1) in the same way as Example 2, and irritation-feeling tests were performed to evaluate the preparations. None of the samples induced irritation feeling.

TABLE 13

| Prescription | |
| --- | --- |
| (Ingredient I) | |
| Dimethicone (10 mPascal · sec) | 8% by mass |
| Dimethicone (50,000 mPascal · sec) | 1% by mass |
| Cyclomethicone (Pentamer) | 22% by mass |
| Sucrose monostearate | 0.5% by mass |
| Squalane | 2% by mass |
| Active Ingredient described in Table 14 | 1% by mass |
| Stearyl glycyrrhetinate | 0.05% by mass |
| alkylenoxide methylsiloxane copolymer (Silicon KF-6017) | 4% by mass |
| (Ingredient II) | |
| Polyethyleneglycol 400 | 1% by mass |
| 1,3-Butanediol | 1% by mass |
| Glycerin | 12% by mass |
| Phenoxyethanol | 0.5% by mass |
| Lipidurer-C | 2% by mass |
| Water | 42.95% by mass |
| (Ingredient III) | |
| Bentone-38V | 2% by mass |

TABLE 14

| Sample | Active ingredients |
| --- | --- |
| Example 19 | Prednisolone |
| Example 20 | Dexamethasone |
| Example 21 | Indomethacin |
| Example 22 | Bufexamac |
| Example 23 | Ibuprofen |
| Example 24 | Hydrocortisol |

INDUSTRIAL APPLICABILITY

The external skin agent of the present invention has an effective inflammatory prevention effect, so that it may be used for preventing onset of skin inflammations. Meanwhile, the external skin agent is extremely low irritant, so that it may be used to prevent the recurrence of onset of skin inflammations following treatment on a daily basis over a long period of time. In addition, when an anti-inflammatory agent is incorporated, the external skin agent of the present invention may be applied to anti-inflammatory quasi drugs or anti-inflammatory skin external medicines.

The invention claimed is:

1. An external skin agent comprising:
   1) 0.1-20 wt % of dimethyl distearyl ammonium chloride hectorite
   2) 0.1-10 wt % polymethacryloyloxyethyl phosphorylcholine further comprising at least three kinds of dimethicones consisting of a volatile dimethicone, a low-viscosity dimethicone, and a middle-viscosity dimethicone wherein the total content of the dimethicone is 20-40% by weight.

2. An external skin agent according to claim 1, further comprising a sucrose fatty acid ester.

3. An external skin agent according to claim 1, further comprising one or two or more kinds of anti-inflammatory components selected from the group consisting of alcohol extract of Compositae *Arctium lappa*, alcohol extract of Araliaceae *Panax Notoginseng*, alcohol extract of Betulaceae *Betula maximowicziana*, alcohol extract of Leguminosae *Sophora flavescens*, alcohol extract of Lamiaceae *Salvia officinalis*, alcohol extract of Juglandaceae *Engelhardtia chrysolepis*, alcohol extract of Compositae *Achillea millefolium*, alcohol extract of Lamiaceae *Rosmarinus officinalis*, glycyrrhizinic acid glycyrrhizinic acid salt, glycyrrhetinic acid ester, ursolic acid ursolic acid salt, ursolic acid ester, phytosterol, indomethacin, ketoprofen, ketotifen, bufexamac, dexamethasone, prednisolone, beclomethasone, betamethasone, hydrocortisol, and tacrolimus.

4. An external skin agent according to claim 1, which is in a form of a water-in-oil emulsion.

5. An external skin agent according to claim 1, which is used for alleviating or reducing the risk of atopic dermatitis.

* * * * *

UNITED STATES PATENT AND TRADEMARK OFFICE
CERTIFICATE OF CORRECTION

PATENT NO. : 8,741,323 B2
APPLICATION NO. : 11/722338
DATED : June 3, 2014
INVENTOR(S) : Yasuhiro Ohara et al.

It is certified that error appears in the above-identified patent and that said Letters Patent is hereby corrected as shown below:

Title page (item 57, Abstract) at line 2, Change "An" to --an--.

In the Drawings

Sheet 1 of 2 (FIG. 1) line 8 (approx.), Change "Tukcy" to --Tukey--.

In the Specification

Column 6 line 22, Change "bymass" to --by mass--.

Column 10 lines 9-14, Delete "Examples of the............structure." and insert the same on Col. 10, line 8, after "surfactant." as the continuation of the same paragraph.

Column 10 line 58, Change "Arallaceae" to --Araliaceae--.

Column 12 line 6, Change "ibota" to --ibotta--.

Column 12 line 65, Change "carageenan," to --carrageenan,--.

Column 13 line 5, Change "calonic" to --colonic--.

Column 13 line 25, Change "laked." to --leaked.--.

Column 15 line 59, Change "δ" to --d-δ- --.

Column 16 line 18, Change "δ" to --d-δ- --.

Column 17 line 7, Change "75" to --75.--.

Signed and Sealed this
Seventeenth Day of February, 2015

Michelle K. Lee
*Deputy Director of the United States Patent and Trademark Office*